Figures 1, 2:
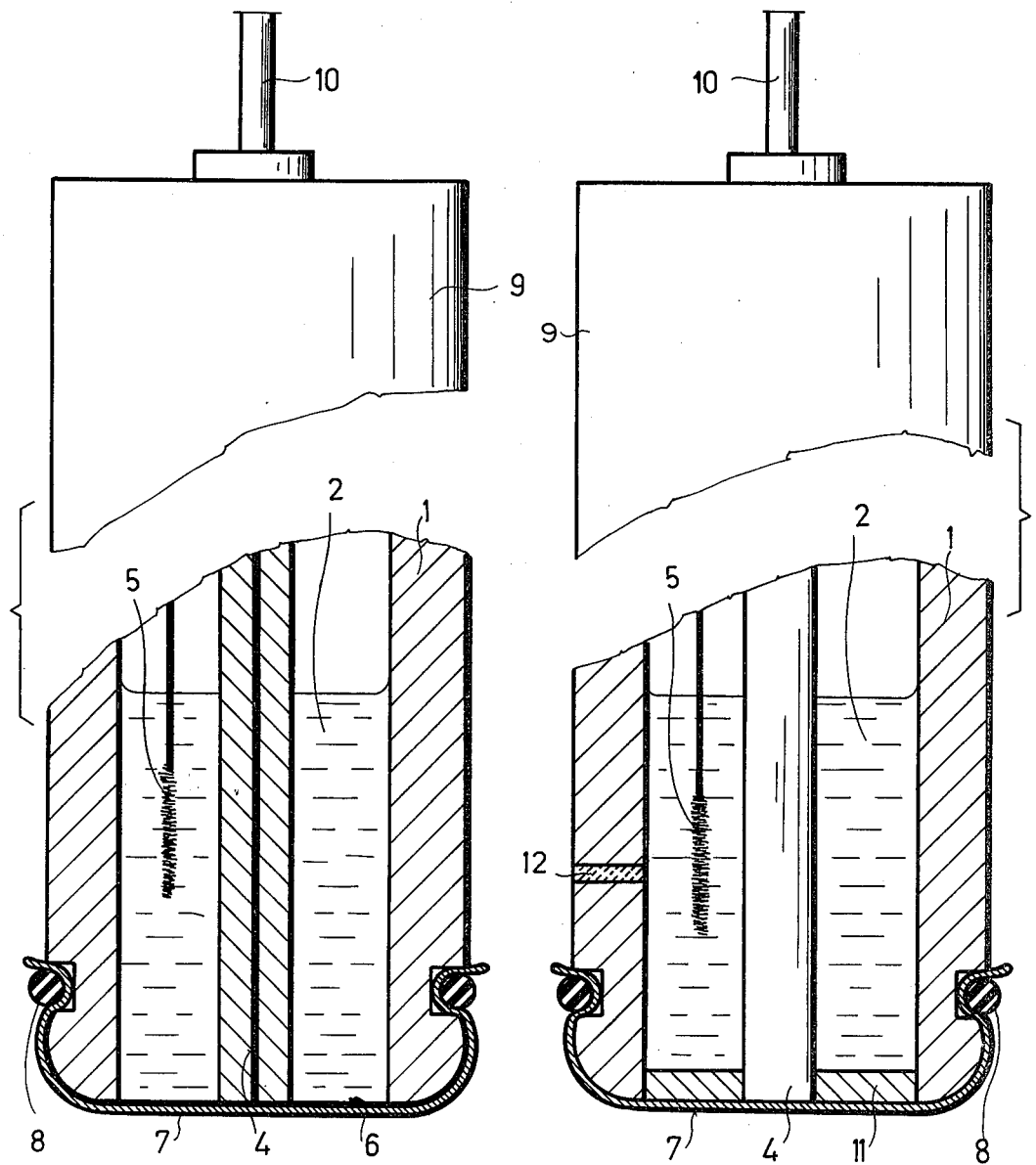

United States Patent [19]

Havas et al.

[11] 4,375,399
[45] Mar. 1, 1983

[54] MOLECULE SELECTIVE SENSOR FOR INDUSTRIAL USE AND PROCEDURE FOR ITS PREPARATION

[75] Inventors: Jenő Havas; Géza Nagy; Emma Porjesz; Ernő Pungor, all of Budapest, Hungary

[73] Assignee: Radelkis Elektrokémiai Miszergyártó Szövetkezet, Budapest, Hungary

[21] Appl. No.: 218,102

[22] Filed: Dec. 19, 1980

Related U.S. Application Data

[63] Continuation of Ser. No. 49,334, Jun. 18, 1979, abandoned.

[30] Foreign Application Priority Data

Sep. 8, 1978 [HU] Hungary .............................. RA 688

[51] Int. Cl.³ .......................... C12Q 1/00; C12Q 1/14
[52] U.S. Cl. ............................ 204/195 B; 204/195 P;
435/14; 435/25; 435/175; 435/177; 435/180; 435/288; 435/817
[58] Field of Search ................ 204/1 E, 195 B, 195 P; 435/817, 288, 175, 177, 180, 14, 25

[56] References Cited

U.S. PATENT DOCUMENTS

| | | | |
|---|---|---|---|
| 3,539,455 | 11/1970 | Clark ........................... | 204/195 P X |
| 3,843,446 | 10/1974 | Vieth et al. ..................... | 435/177 X |
| 3,896,008 | 7/1975 | Keyes ................................ | 204/1 T |
| 4,020,830 | 5/1977 | Johnson et al. ............. | 204/195 B X |
| 4,066,512 | 1/1978 | Lai et al. .......................... | 435/288 X |
| 4,069,106 | 1/1978 | Stanley et al. ...................... | 435/177 |
| 4,092,219 | 5/1978 | Lin et al. .......................... | 435/177 X |

FOREIGN PATENT DOCUMENTS 52-47983  4/1977  Japan .................................. 435/180

OTHER PUBLICATIONS

C & EN, p. 16, Oct. 9, 1978.

*Primary Examiner*—G. L. Kaplan
*Attorney, Agent, or Firm*—Gabriel P. Katona

[57] ABSTRACT

A molecule selective sensor having two permeable membranes in contacting relationship with each other, one membrane being a protein membrane found in nature, as for example, hog intestine membrane, air bladder of fish, epidermal section of mammals and reptiles, etc. and the other membrane being the reaction product of acrylamide, polyvinylalcohol, an enzyme, bovine albumin and glutaric aldehyde.

5 Claims, 2 Drawing Figures

MOLECULE SELECTIVE SENSOR FOR INDUSTRIAL USE AND PROCEDURE FOR ITS PREPARATION

This is a continuation of application Ser. No. 49,334, filed June 18, 1979 and now abandoned.

The invention relates to an industrial selective electroanalytical sensor, which is suitable for the selective analysis of ions and compounds e.g. dichlorphenols, cyanides, mercuric ($Hg^{II}$) ions dissolved in liquids e.g. industrial sewages, and it relates to the procedure for the preparation of molecule selective electroanalytical sensors.

Among the molecule selective electroanalytical sensors, the so called enzyme electrodes are well known, which are suitable for the determination of the concentration of compounds dissolved in liquid samples.

The literature (P. L. Baley: Analysis with selective electrodes, Heyden and Son Ltd. London 1976, Nagy C., Pungor, E.: Hung. Sci. Instr. 32, 1–10/1975/) discusses in details the electrochemical behaviour and the application of the molecule selective sensors. It is a common property of the known molecule selective sensors which can be considered as electroanalytical measuring cells that their electrode body holding an ion selective or metal sensing electrode and a reference electrode are placed in a tubular body containing electrolyte solution. The end of this tubular body on the side of the sensing electrode is closed by a gas or dissolved material permeable film e.g. dialysis membrane, which is in contact with a layer containing selective and action specific catalyst for the component to be determined; physically or chemically immobilized enzyme, so called reaction layer e.g. polyacrylamide-gel layer; or in turn with: gas or gas and dissolved component permeable film e.g. cellophane film, with solution-layer containing selective enzyme in suspension, as reaction layer; gas or gas and dissolved component permeable film e.g. cellophane film.

A Hungarian patent is also known (No. 7577 1978) in the case of which the reaction layer is a protein based natural membrane containing enzyme immobilized with chemical bond.

The known molecule selective sensors operates that way, that the component to be determined, the so called substrate, e.g. glucose molecules, and in given case the reagent e.g. oxygen molecules, enter by diffusion into the reaction layer containing selective enzyme as a reaction specific catalyst e.g. glucose-oxidase, and there produce a chemical reaction. The sensing electrode gives a signal which is in a well defined relationship with the concentration or activity of one or other component taking part in the reaction or produced in it. The local value of the mentioned concentration or activity—if all other important parameters remain constant—depends on the reaction rate which is in a well defined dependence with the concentration of the substrate. This way measuring the electric current intensity or cell voltage signal given by the enzyme electrode at steady-state conditions the sample concentration value directly can be determined.

The preparation of known molecule selective sensors is a circuitous, time consuming procedure and requires special training and knowledge and it is also only more or less reproducible in spite of the fact, that there are available a very large number of different methods for solving the problem of enzyme immobilisation. (O. R. Zaborsky: Immobilized Enzymes, CRC. Press. Cleveland, Ohio 1974).

The most disadvantageous property of the sensors is their short life time, which is related to the unfavourable construction and formation of the reaction layer.

Another drawback is that the sensor or the enzyme containing gel-layers must be stored at low temperature e.g. $-1°\ldots +2°$ C. to prolong their activity.

The known electrodes are easily damaged, their mechanical stability is slight and their response time is long e.g. 2 to 8 minutes, all of which hinder their application in laboratory and mainly in industrial use.

It is an advantage of the sensor in accordance with the invention that it eliminates the enzyme action inhibiting effect caused by the silver ions coming from the reference electrode.

The object of the invention is to provide an industrial molecule selective sensor which can be prepared simply without special knowledge in a short time, in a reproducible way; which further has high mechanical stability, the life time of which is several times higher than that of the known sensors e.g. 1 year, and the response time of which is short e.g. 40 ... 60 seconds.

The invention is based on that discovery that an improved sensor can be prepared in that its reaction layer is formed on protein based natural film which is found in nature e.g. intestinal membrane, or on synthetic e.g. polypropylene film; or in a net made of protein like material e.g. silk net; or in a synthetic net e.g. polyester net used as carrier; from a net in the net structured membrane containing covalently bound carrier free enzyme catalyst or catalysts being with the latters in chemical or physical bond. The net in the net structured membrane is basically a cross linked synthetic e.g. polyacrilamide, or polyvinylchloride film, in the inert cross linked net of which an active cross linked net consisted of inert protein and or enzyme molecules takes place.

The stability of the sensor according to the invention is excellent owing to its structure, further on to the similar to the enzymes chemical properties and good mechanical stability of the carrier materials, and to the condition of the enzyme being linked with physical or chemical bonds to the carrier. The chemical resistance and stability of the enzymes immobilized in the described way in the membrane is similarly excellent—accordingly the sensor is capable to function for long time, being out of use—in given case even at room temperature—it can be stored for long time e.g. one year without noticeable change of its activity. The physical chemical properties of enzymes included in the net in the net structured reaction layer also are advantageously changed in that they are active over a larger pH range than the native enzymes themselves.

It is a further advantage of the membrane according to the invention that its solidity, and the concentration of the immobilized enzymes in it, can be varied at will.

The water-, gas-, and ion permeability of the natural based membranes used as carriers (air bladder of fish, epidermis section of mammals or reptiles, intestinal membrane or cornea of certain animal species) is ideal from a measuring point of view. It is a further useful property of them, that beside providing the permeability for gases, or ions playing role as reagent or reaction product, they behave as an impermeable barrier to compounds of high molecular weight which may interfere with the measurement. These can be the substrate itself or other components in the sample.

The sensor in accordance with the invention can be prepared also as a reaction layer wherein a membrane is used which contains two or more different reaction layers or which is made of two or more different enzyme containing membranes disposed one over the other.

In this arrangement each membrane surface contains different enzymes in immobilized form. In case of the selective β-glucoside sensor the membrane surface contacting the sample contains β-glucosidase enzyme while the membrane at the side of the sensing electrode contains glucose oxidase. The enzyme on the first membrane, the β-glucosidase catalyses a hydrolysis reaction between the component to be determined, that is β-glucoside (e.g. amygdaline, or salicine) and water, one of the products of which is glucose. The glucose oxidase enzyme on the other membrane catalyses the reaction between the produced glucose and oxygen. The oxygen provides on the sensing electrode located behind the membranes a measuring signal proportional to its concentration.

The signal proportional to the decrease in oxygen concentration is proportional to the concentration of the component to be determined.

Using this arrangement measuring technical simplifications and increase of selectivity can be achieved; also components can also be determined which don't give in a one step enzyme reaction an electroanalytically well determinable product, or change in the concentration or activity of a detectable species.

The sensor of the invention can be constructed also such that in discrete areas of the reaction layer forming membrane, or natural structured film, different kinds of enzymes are immobilized in statistically homogeneous distribution and to these discrete areas are attached one or more sensing electrodes. This arrangement enables to prepare multifunction molecule selective sensors without increase of the dimensions, whereby the analysis of more components can be accomplished simultaneously in the same sample, or by measuring simultaneously the concentration of components interfering with the measurements their effect can be accounted automatically or manually.

In other variations of the invention to further protect against mechanical effects and to further increase the mechanical stability of the reaction layer inert plastic net or tissue is placed in contact with the membrane. In other versions—to achieve very short response time—in the surface layer of one side of the membrane gas permeable or ion exchanger type layer is formed by cross linkage after an impregnation process.

The molecule selective sensors of the invention can be prepared so that solution of monomer or polymers e.g. acrylamide capable to form inert cross linked net and or that of polyvinylalcohol is mixed with the buffered solution of the inert protein capable to form active cross linked net and or the solution of enzyme e.g. serum protein and glucose oxidase. Into the solution mixture is further added bifunctional cross linking agent e.g. N,N'-methylene-bis acrylamide and glutaric aldehyde, initiator e.g. persulphate ions, and additives e.g. ferrosulphate and glycerin. The solution mixture is spread on protein based natural membrane e.g. on intestinal membrane or on plastic e.g. polypropylene film placed on smooth surface or on tissue net e.g. silk net, or on inert plastic net e.g. nylon net or on the smooth surfaced object itself. After the cross linking and the drying processes of the solution mixture the formed self-supporting membranes are separated from the smooth surfaced object and placed in a bath of distilled water where any soluble components are dissolved out. The membranes are then ready for use.

The prepared membrane together with the gas or dissolved component permeable film is placed on the covering body of the sensor, the sensing and the reference electrode are immersed in the electrolyte solution and the surface of the sensing electrode in the immediate vicinity of the membrane. The electrodes are attached and the sensor is then in condition for use.

FIG. 1 diagramatically shows an open bottomed sensor according to the present invention and described in greater detail in Example 1.

FIG. 2 illustrates diagramatically a similar sensor as in FIG. 1 with the addition of a disc shaped insulating layer in the bottom of the container and affixed to the sensing electrode to avoid undue movement. A more detailed description of this drawing is provided in Example 2.

EXAMPLE 1

The end of covering body 1 is closed with gas permeable polypropylene film 6 being in contact with the sensing electrode 4.

Membrane 7—which is constructed from active net containing albumin and glucose oxidase enzyme (E.C. 1.1.3.4.) cross linked with glutaric aldehyde and placed in inert net of polyvinylalcohol cross linked with N,N'-methylene bis-acrylamide chemically bound to commercial hog intestinal membrane—is in contact with gas permeable film 6. Gas permeable film 6 and membrane 7 are fixed to the covering body 1 by rubber ring 8. The other end of covering body 1 is closed by electrode cap 9.

Cable 10 contacted with sensing electrode 4 and reference electrode 5 is connected to the inputs of polarizing power source and current intensity measuring circuit.

The preparation of the glucose selective sensor is made in the following way: A given part of salted, commercially available hog intestinal membrane is soaked in distilled water for 10 ... 15 minutes. The swollen membrane together with 15μ thick gas permeable polypropylene membrane is fixed in stretched out state on the end of the covering body of the sensor. (The polypropylene membrane must be on the side of the cave of covering body.) The membrane is allowed to dry for 20 minutes.

80 mg. bovine albumin, 80 mg. glucose oxidase (SIGMA Chemical Company, Type II) and 100 mg. N,N'-methylene-bis-acrylamide are weighed into a beaker and is dissolved shaking in 5 ml pH=7.08 buffer solution. 2.97 g. of 10% (w/w) polyvinyl alcohol is weighed in another beaker. After this, 0.3 g. glycerin is added into the solution being in the first beaker, while into the solution of the other beaker 100 μl of 25% glutaraldehyde solution, 100 μl of 5% freshly prepared ferrosulfate solution are added. Both are mixed, after that the two solutions are unified and mixed again. 2 .. . 3 mg. potassium persulfate is added to the mixture, it is homogenized and 40 μl or 2 ml. of it is spread on 8 $cm^2$ surface area respectively of the hog intestinal membrane, or smooth surfaced plastic sheet, or polypropylene membrane. After a rest at room temperature for 12 hours the soluble non-immobilized enzyme and glutaraldehyde excess is removed from the membranes being on the end of the covering body or being separated from the plastic surface by washing them with distilled water.

The membrane prepared this way, contains immobilized glucose oxidase and is ready for measuring or storage.

After preparing the active membrane the platinum sensing electrode placed in carrier body in the said way is prepared, or conditioned. The measuring surface of the sensing electrode is soaked in 6 moles/dm$^3$ nitric acid dropped on glass plate surface for 2 to 3 minutes.

The nitric acid is rinsed with distilled water. After the rinsing the sensing electrode is ready for use. (The washing with nitric acid must be repeated every 2 to 3 weeks during the measurements.)

After the preparatory procedures the glucose selective sensor is put together according to FIG. 1, and it is connected to the polarizing power source and galvanometer unit.

The determination of the unknown sample concentration can be done using calibration curve or addition method. In the following an advantageous version of the addition method the serial sample addition method is described.

It has been concluded that between the measured decrease in current intensity ($\Delta i$) and the glucose concentration of the solution (c) the following relationship exists:

$$\Delta i = k \frac{v}{1 + \frac{K}{c}} \quad (1)$$

where v is the maximal reaction rate
K the Michaelis constant of the enzyme substrate complex
k rate constant.

Measuring the current decrease in two solutions of known glucose concentration the values v and k valid for the given circumstances are determined, on the basis of which the concentration of the solution containing the n-th sample can be calculated from the measured current intensity decrease according to the followings:

$$c_n = i_n k \frac{(c_{n-1} + k)^2}{k + v} \quad (2)$$

On the basis of equation (2) the concentration of the sample is:

$$c'_n = c_n \frac{V_A + 2a_n}{a_n}$$

where $a_n$ is the volume of the n-th sample
$V_a$ the volume of the solution after the addition of the standards.

Other molecule selective sensors also can be prepared according to the method of the Example.

In table 1 further examples are shown.

The first column of the table gives the molecule, selectively measurable with the sensor; the second column lists the enzyme immobilized in the membrane in contact with the gas permeable film while in the third column the type of the sensing electrode is given.

TABLE 1

| Component to be determined | Immobilized enzyme | Sensing electrode |
|---|---|---|
| uric acid | uricase E.C.1.7.3.3. | Platinum |
| cholesterine | cholesterine oxidase E.C.1.1.3.6. | " |
| L-amino acid | L-amino acid oxidase E.C.1.4.3.2. | " |
| D-amino acid | D-amino acid oxidase E.C.1.4.3.3. | " |
| D-galactose | Galactose oxidase E.C.1.1.3.9. | " |
| sulfite | sulfite oxidase E.C.1.8.3.1. | " |
| oxalate | xanthyne oxidase E.C.1.2.3.4. | platinum |
| xanthyne | xanthyne oxidase E.C.1.2.3.2. | " |
| o-diphenol | o-diphenol oxidase E.C.1.10.3.1. | " |
| p-diphenol | p-diphenol oxidase E.C.1.10.3.2. | " |
| hydrogenperoxide | catalase E.C.1.11.1.6. | " |
| lactate | lactate oxidase E.C.1.1.3.2. | " |
| piruvate | piruvate oxidase E.C.1.2.3.3. | " |
| alcohol | alcohol oxidase E.C.1.1.3.1.3. | " |
| L-phenylalanine | phenylalaninase E.C.1.14.3.1. | " |
| 2-oxocarbonic acid | piruvate decarboxylase E.C.4.1.1.1. | hydrogen ion selective electrode e.g. glass electrode |
| oxalic acetate | oxalic acetate decarboxylase E.C.4.1.1.3. | hydrogen ion selective electrode e.g. glass electrode |
| acetoacetic acid | acetoacetate decarboxylase E.C.4.1.1.4. | hydrogen ion selective electrode e.g. glass electrode |
| L-valine | valine decarboxylase E.C.4.1.1.14. | hydrogen ion selective electrode e.g. glass electrode |
| L-glutamate | glutamate decarboxylase E.C.4.1.1.15. | hydrogen ion selective electrode e.g. glass electrode |
| L-ornithine | ornithine decarboxylase E.C.4.1.1.17. | hydrogen ion selective electrode e.g. glass electrode |
| L-lysine | lysine decarboxylase E.C.4.1.1.18. | hydrogen ion selective electrode e.g. glass electrode |
| penicilline | β-lactamase I E.C.3.5.2.6. | hydrogen ion selective electrode e.g. glass electrode |

EXAMPLE 2

FIG. 2 shows—partly intersected—the form prepared according to the example of the urea-selective sensor of the invention. Inside covering body 1 is placed electrolyte solution 2 containing chloride ions, in which are immersed sensing electrode 4 and silver-silver chloride reference electrode 5 disc shaped insulating layer 11 fixes sensing electrode 4 in the end of covering body 1 with a bonding impermeable for the electrolyte solution 2; membrane 7 which contains immobilized urease enzyme (E.C.3.5.1.5.) silk or plastic net, or which is free of carier net in the net structure, is in contact with the covering body 1. The self-supporting membrane 7 is fixed to the covering body with rubber ring 8. Inside the wall of covering body 1 filter layer 12, e.g. ceramic bar permeable for electrolyte 2 is placed. The other side of covering body 1 is closed with plastic electrode cup 9. Cable 10 connected to sensing electrode 4 and reference electrode 5 is in connection with the inputs of electronic voltage measuring apparatus.

The preparation of the reaction layer of the urea selective sensor is done as it is given in description of Example 1. Differences are that in the membrane urease enzyme (E.C.3.5.1.5.) is immobilized and instead of hog intestinal membrane silk or nylon net is used. The sensor is assembled in a manner shown in FIG. 2. The determination of the concentration of the component to be measured can be accomplished using cell voltage—concentration calibration curve or using addition method in the well known way.

Different other molecule selective sensors of the Example 2 also can be accomplished. In Table 2 are given a few further example summarized. In the first column of the table the molecule, selectively measurable with the sensor is given, in the other column the enzyme immobilized in the membrane is listed while in the third one the type of the sensing electrode to be used is given.

TABLE 2

| Component to be determined | Immobilized enzyme | Sensing electrode |
| --- | --- | --- |
| L-dioxyphenylalanine | L-amino acid oxidase E.C.1.4.3.2. | Ammonium ion selective electrode |
| L-phenylalanine | L-amino acid oxidase E.C.1.4.3.2. | Ammonium ion selective electrode |
| L-amino acids | L-amino acid oxidase E.C.1.4.3.2. | Ammonium ion selective electrode |
| D-serine | D-serine dehydratase E.C.4.2.1.14. | Ammonium ion selective electrode |
| L-homoserine | homoserine dehydratase E.C.4.2.1.15. | Ammonium ion selective electrode |
| L-threonine | threonine dehydratase E.C.4.2.1.16. | Ammonium ion selective electrode |
| L-hystidine | hystidinase E.C.4.3.1.3. | Ammonium ion selective electrode |
| nitrite | nitrite reductase E.C.1.6.6.4. | Ammonium ion selective electrode |

EXAMPLE 3

The construction of the arginine selective sensor of the invention prepared according to the Example is basically identical with the construction of the urea selective sensor. The difference is that two membranes 7—one covering the other—are fixed with ring 8 on the end of covering body 1, on the surface of membrane being on sensing electrode 4 side enzyme urease while on the surface of the other membrane perforated enzyme arginase is bound in immobilized form. This way the arginine selective sensor is formed with two reaction layers.

The preparation of the arginine selective sensor is done in the following way: First the urea selective sensor is prepared as it is given in Example 2. After that on the surface of the urease enzyme containing membrane another perforated membrane containing arginase enzyme (E.C.3.5.3.1.) is placed. The preparation of the latter is done identically as it is described in Example 1.

The arginine selective sensor can also be made wherein only one membrane 7 is used in which, in statistically homogeneous distribution, two kinds of enzymes, arginase and urease are immobilized. In case of this version the further construction and preparation of the sensor consequently are identical with those described at version earlier discussed.

The function of the sensor is based on a two step chemical reaction:

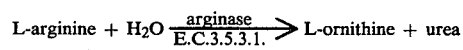

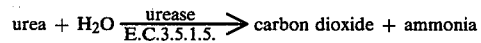

The determination of the concentration of arginine to be measured is done in the well known way using calibration curve or addition method. A survey is given in Table 3 about the molecule selective sensors of the invention which can be prepared with two reaction layers or with a reaction layer containing two kinds of enzymes in statistically homogeneous distribution similarly to Example 3. In the first column of the Table is listed the molecule, to be determined; the second column gives the enzyme catalyst immobilized in the external membrane. The third column shows the enzyme catalysts immobilized in on the internal membrane being in the side of the sensing electrode. In the fourth column the appropriate sensing electrodes are listed.

TABLE 3

| Component to be determined | Enzyme immobilized first kind | second kind | Sensing electrode |
| --- | --- | --- | --- |
| inosine | uridine nucleosidase E.C.3.2.2.2. | xanthine oxidase E.C.1.2.3.2. | platinum electode |
| adenosine | adenosine nucleosidase E.C.3.2.2.a. | adenine deaminase E.C.3.5.4.2. | ammonium, ion hydrogen ion selective |
| guanosine | guanosine phosphorilase E.C.2.4.2.15. | guanase E.C.3.5.4.3. selective | ammonium, ion hydrogen ion |
| guanine | guanase E.C.3.5.4.3. | xanthine oxidase E.C.1.2.3.2. | platinum electrode |
| creatinine | creatininase E.C.3.5.3.3. | urease E.C.3.5.1.5. | ammonium ion selective electrode |
| β-D-glucosides disaccharides amygdaline salicine | β-clucosidase E.C.3.2.1.21. | glucose oxidase E.C.1.1.3.4. | platinum electrode |
| α-D-glucosides e.g. maltose | α-glucosidase E.C.3.2.1.20. | glucose oxidase E.C.1.1.3.4. | platinum electrode |
| D-glucose-1-phosphate | glucose-1-phosphatase E.C.3.1.3.10. | glucose oxidase E.C.1.1.3.4. | platinum electrode |
| D-glucose-6-phosphate | glucose-6-phosphatase E.C.3.1.3.9. | glucose oxidase E.C.1.1.3.1. | platinum electrode |
| barbiturate | barbiturase E.C.3.5.2.1. | urease E.C.3.5.1.5. | ammonium or hydrogen ion selective electrode |

EXAMPLE 4

In the 4th Example the model form and the preparation of the bifunctional molecule-selective sensor is described.

Two platinum sensing electrodes 4 built in carrier body 3 are placed in chloride ion containing electrolyte buffer solution 2 contained in covering body 1. Gas permeable polypropylene film 6 fixed on the opening of covering body 1 is in contact with the surfaces of sensing electrodes 4. The surface of film 6 is covered with film 7. In that side of membrane 7 which is in contact with the first sensing electrode 4 there is present enzyme D-amino acid oxidase, while in the other side contacted with the second sensing electrode 4 enzyme L-amino acid oxidase is bound in immobilized form. The construction of the bifunctional molecule selective sensor concerning the further details is consequently similar to that of the sensor described in the Example 1.

The preparation of the reaction layers containing amino acid oxidase is basically done as it is described in Example 1, the difference is that instead of hog intestinal membrane thin skin tissue is used, and, instead of glucose oxidase in the first membrane part, there is present 2–3 mg. D-amino acid oxidase enzyme (E.C.1.4.3.3., Sygma, chrystalline) used at pH 8.3 while in the other part 2–3 mg. L-amino acid oxidase enzyme (E.C.1.4.3.2., Sygma, IV.) is immobilized. The further steps concerning the preparation of the sensor consequently are identical with those described in Example 1.

With the bifunctional molecule selective sensor described it is possible to determine selectively D- and L-amino acid isomers in samples containing both species. In carrying out the measurement the selective sensor is first calibrated with standard solutions of the first amino acid to be measured, e.g. L-phenylalanine, then afterward with that of the other amino acid isomer e.g. D-phenylalanine. To calibrate the electrode the electrode is taken out of a solution of phosphate buffer (pH=8) stirred intensively and dipped in one of the standard solutions of the same pH using stirring of the same intensity and employing a polarizing voltage of −0.6 V, the change of the current intensity ($\Delta i$) is measured.

Plotting the measured values of $\Delta i$ against the concentrations of the standard solutions the two calibrations curves are prepared by means of which the concentration of the different amino acids, the ratio of the two optical isomers can be determined after measuring $\Delta i$.

The use of the selective sensor constructed according to the Example is very advantageous in case of studying the effectivity of optical isomers resolving processes.

The addition method described in connection with the Example 1 also can be used for determination of the ratio of amino acid isomers. Similarly to Example 4 several other advantageously applicable bifunctional molecule selective sensors of the invention can be prepared.

A survey of them is given in Table 4.

In the second column of the table the name of the enzyme immobilized in the first surface portion is listed while in the fourth column the enzyme immobilized in the other part of the membrane is given.

TABLE 4

| component to be determined | enzyme immobilized in the first part of the membrane | component to be determined | enzyme immobilized in the second part of the membrane |
|---|---|---|---|
| glucose | glucose oxidase E.C.1.1.3.4. | alcohol | alcohol oxidase E.C.1.1.3.1.9. |
| glucose | glucose oxidase E.C.1.1.3.4. | mannose | hexose oxidase E.C.1.1.3.5. |
| urea | urease E.C.3.5.1.5. | creatinine | creatininase E.C.3.5.3.3. urease E.C.3.5.1.5. |
| glucose | glucose oxidase E.C.1.1.3.4. | uric acid | uricase E.C.1.7.3.3. |
| glucose | glucose oxidase E.C.1.1.3.4. | L-phenylalanine | phenylalaninase E.C.1.14.3.1. |
| urea | urease E.C.3.5.1.5. | arginine | arginine decarboxylase E.C.4.1.19. |
| glucose | glucose oxidase E.C.1.1.3.4. | amygdaline | β-glucosidase E.C.3.2.1.21. glucose oxidase E.C.1.1.3.4. |

EXAMPLE 5

In Example 5 the construction and method of preparation of a multifunctional molecule selective sensor of the invention is described which can be used for the selective determination of certain amino acids in the presence of others.

The construction of the multifunctional sensor is similar to that of the bifunctional sensor described in Example 4; there is a difference that it does not contain gas-permeable film 6, and in the electrolyte solution 2 three hydrogen ion selective glass sensing electrodes 4 are placed, in three separated parts of the membrane 7, each being in contact with another sensing electrode 4, there are three different immobilized amino acid decarboxylases; L-lysine decarboxylase, L-thyrosine decarboxylase, and L-phenylalanine decarboxylase.

The preparation of the sensor and the reaction layers are made identically to those described in Example 4.

With the above molecule selective sensor the L-thyrosine, L-lysine, L-phenylalanine content of amino acid containing samples can be determined selectively. The determinations can be made using three different cell voltage-amino acid concentration calibration curves, each of them referring to one of the amino acids respectively.

Similarly, other versions also can be prepared. The different individual reaction layer fields can contain the following enzymes in immobilized form: L-arginine decarboxylase, L-glutamic acid decarboxylase, L-glutamine decarboxylase, L-hystidin decarboxylase, and urease.

What we claim is:

1. A process for producing an enzymatically active membrane which consists in mixing together 1–20 weight percent of acrylamide, 1–20 weight percent of polyvinylalcohol, 0.01–10 weight percent of bovine albumin, 0.0001–5 weight percent of an enzyme, 0.1–5 weight percent of glutaric aldehyde, a polymerization initiating amount of potassium persulfate and the remainder to 100 weight percent of distilled water, spreading the mixture on a protein membrane found in nature to form a thin sheet and allowing the mixture to react for 12 hours at room temperature.

2. A process as claimed in claim 1 wherein the mixture contains in addition 0.1–5 weight percent of N,N'-methylene-bis-acrylamide.

3. A hollow molecule-selective sensor having a sensing electrode and a reference electrode and two permeable membranes in contacting relationship with each other, one of said membranes being a protein membrane found in nature and the other of said membranes being a self-supporting enzymatically active membrane prepared according to the process of claim 1.

4. A sensor as claimed in claim 3 wherein the said protein membrane found in nature is selected from the group consisting of hog intestine membrane, air bladder of fish, epidermal section of a mammal, epidermal section of a reptile and corneal section.

5. A sensor as claimed in 3 wherein the self-supporting enzymatically active membrane comprises two or more enzymes.

* * * * *